(12) United States Patent
Suzuki

(10) Patent No.: US 10,426,354 B2
(45) Date of Patent: Oct. 1, 2019

(54) OBJECT INFORMATION ACQUIRING APPARATUS

(71) Applicant: CANON KABUSHIKI KAISHA, Tokyo (JP)

(72) Inventor: Koichi Suzuki, Kodaira (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 562 days.

(21) Appl. No.: 14/830,876

(22) Filed: Aug. 20, 2015

(65) Prior Publication Data

US 2016/0058294 A1 Mar. 3, 2016

(30) Foreign Application Priority Data

Aug. 27, 2014 (JP) .................. 2014-172983

(51) Int. Cl.
*A61B 5/00* (2006.01)
*A61B 8/08* (2006.01)

(52) U.S. Cl.
CPC .......... *A61B 5/0095* (2013.01); *A61B 5/0091* (2013.01); *A61B 5/4312* (2013.01); *A61B 5/7207* (2013.01); *A61B 8/0825* (2013.01)

(58) Field of Classification Search
None
See application file for complete search history.

(56) References Cited

U.S. PATENT DOCUMENTS

| 9,074,991 | B2 | 7/2015 | Suzuki | G01N 21/1702 |
| 9,766,211 | B2 | 9/2017 | Oishi | |
| 2007/0016024 | A1* | 1/2007 | Simopoulos | A61B 8/08 600/437 |
| 2011/0231160 | A1 | 9/2011 | Suzuki | 702/189 |
| 2011/0306865 | A1* | 12/2011 | Thornton | A61B 5/0059 600/407 |

(Continued)

FOREIGN PATENT DOCUMENTS

| CN | 102223840 A | 10/2011 |
| CN | 103354731 A | 10/2013 |

(Continued)

OTHER PUBLICATIONS

Office Action dated Jul. 18, 2018 in counterpart CN application 201510518968.8 (19 pages).

(Continued)

*Primary Examiner* — Bill Thomson
*Assistant Examiner* — Farouk A Bruce
(74) *Attorney, Agent, or Firm* — Venable LLP

(57) ABSTRACT

An object information acquiring apparatus includes: a receiving element configured to receive an acoustic wave generated by emission of light from a light source on an object and output an electric signal; an amplifying unit configured to amplify the electric signal; a scanning unit configured to move relative positions of the receiving element and the object; a controlling unit configured to determine a gain of the amplifying unit according to time when the receiving element receives the acoustic wave; and a processing unit configured to acquire characteristics information on the object, using the electric signal. The controlling unit determines the gain of the amplifying unit according to a positional relation between the receiving element and the object.

23 Claims, 5 Drawing Sheets

(56) References Cited

U.S. PATENT DOCUMENTS

| | | |
|---|---|---|
| 2012/0209104 A1 | 8/2012 | Suzuki .......................... 600/407 |
| 2012/0243369 A1 | 9/2012 | Sudo et al. |
| 2013/0312526 A1 | 11/2013 | Oishi .............................. 73/620 |
| 2014/0051969 A1 | 2/2014 | Suzuki .......................... 600/407 |
| 2014/0187903 A1* | 7/2014 | Oyama ................ A61B 5/6852 600/407 |
| 2014/0221810 A1* | 8/2014 | Kacprowicz ......... A61B 5/0095 600/407 |
| 2015/0005599 A1 | 1/2015 | Suzuki .......................... 600/328 |
| 2017/0156601 A1 | 6/2017 | Sudo et al. |
| 2017/0350869 A1 | 12/2017 | Oishi |

FOREIGN PATENT DOCUMENTS

| | | | |
|---|---|---|---|
| CN | 103908295 A | 7/2014 | |
| EP | 2742854 A1 * | 6/2014 | ........... A61B 5/0095 |
| JP | 2011-152273 A | 8/2011 | |
| JP | 2012-179348 | 9/2012 | |
| JP | 2014128319 A * | 7/2014 | ........... A61B 5/6852 |

OTHER PUBLICATIONS

Office Action dated May 8, 2018 in counterpart JP application 2014-172983 (6 pages).

* cited by examiner

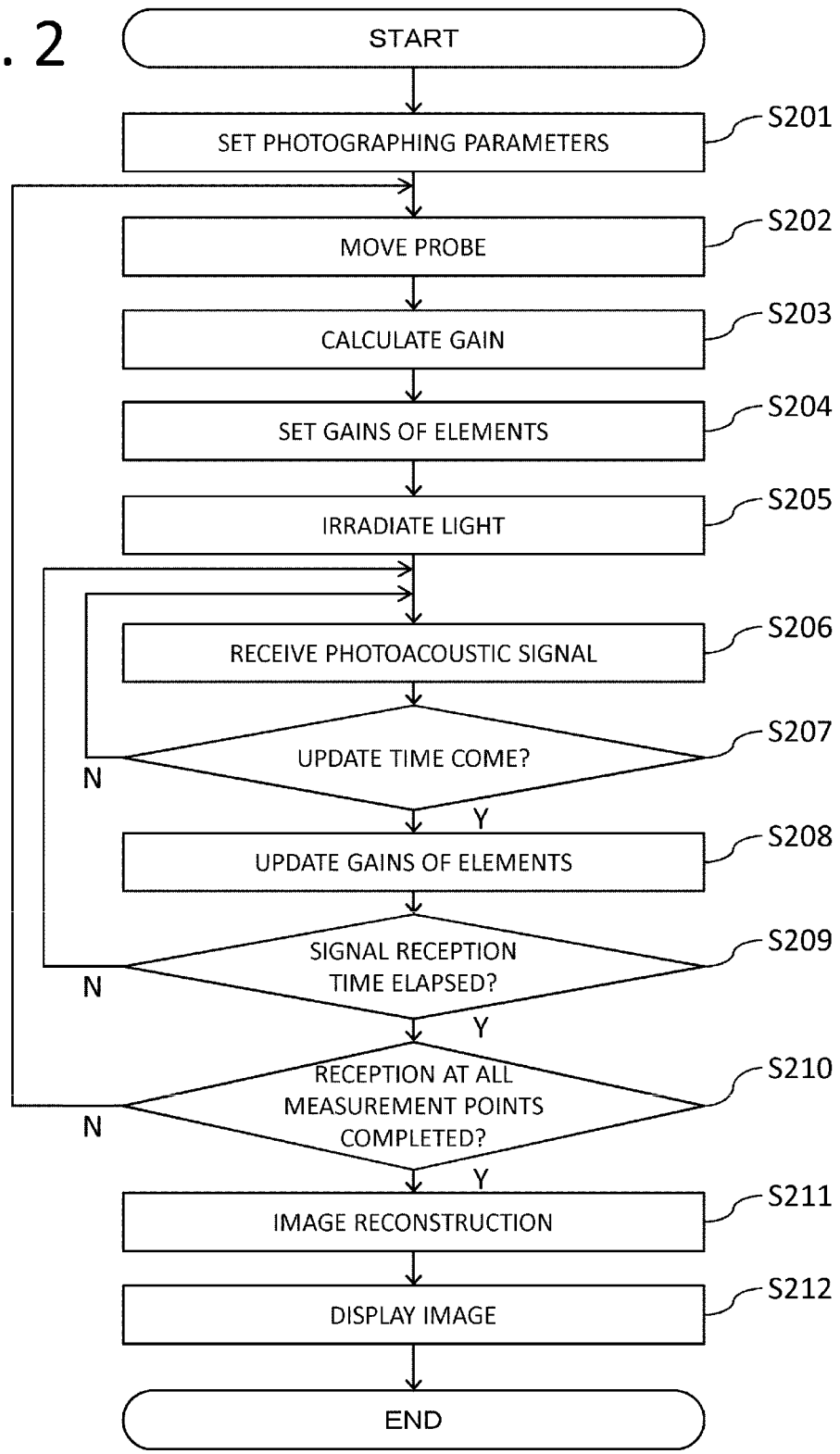

OBJECT INFORMATION ACQUIRING APPARATUS

BACKGROUND OF THE INVENTION

Field of the Invention

The present invention relates to an object information acquiring apparatus.

Description of the Related Art

Mainly in the medical field, an object information acquiring apparatus that irradiates pulsed light on an object, receives, with a probe, an acoustic wave generated from the inside of the object, and visualizes a form and a function on the inside of the object has been studied. When a user of the apparatus starts an imaging of the object, first, a controller in the object information acquiring apparatus sends a signal to a driving circuit of a light source and causes the driving circuit to irradiate pulsed light. When the pulsed light is absorbed by a light absorbing body on the inside or the surface of the object, an acoustic wave is generated by a photoacoustic effect. The acoustic wave is converted into an electric signal called photoacoustic signal by the probe. The controller amplifies the photoacoustic signal, performs signal processing and image reconstruction processing, and presents a diagnostic image to the user.

As the object information acquiring apparatus, there has been proposed an object information acquiring apparatus of a type for receiving an acoustic wave while scanning a probe. For example, in Japanese Patent Application Laid-Open No. 2012-179348, a probe including a receiving element group disposed on a spherical surface scans three-dimensionally the periphery of an object to reduce variation in resolution. In the apparatus, a space between the probe and the object are filled with an impedance matching material to allow an acoustic wave generated in the object to efficiently reach the probe.

On the other hand, in the field of an ultrasonic diagnostic apparatus, processing for changing a gain of an amplifying unit according to reception time of an acoustic wave and correcting attenuation of the acoustic wave is generally performed. This processing is referred to as a time-gain-control (TGC) and a curve indicating a relation between time and a gain is referred to as gain curve.

Patent Literature 1: Japanese Patent Application Laid-Open No. 2012-179348

SUMMARY OF THE INVENTION

In the object information acquiring apparatus described in Japanese Patent Application Laid-Open No. 2012-179348, when the object or the probe is scanned, a positional relation from the receiving elements on the probe to the object changes. Consequently, a magnitude of attenuation of the acoustic wave generated inside the object before reaching the receiving elements also changes during the scanning. When a diagnostic image of the inside of the object is generated using the acoustic wave, variation in contrast is likely to occur.

The present invention has been devised in view of such a problem and it is an object of the present invention to suppress variation in contrast of generated image data in an object information acquiring apparatus that receives an acoustic wave while scanning a probe.

The present invention provides an object information acquiring apparatus comprising:

a light source;

a receiving element configured to receive an acoustic wave generated by emission of light from the light source on an object and output an electric signal;

an amplifying unit configured to amplify the electric signal;

a scanning unit configured to move relative positions of the receiving element and the object;

a controlling unit configured to determine a gain of the amplifying unit according to time when the receiving element receives the acoustic wave; and a processing unit configured to acquire characteristics information on the object, using the electric signal, wherein the controlling unit determines the gain of the amplifying unit according to a positional relation between the receiving element and the object.

The present invention also provides an object information acquiring apparatus comprising:

a light source configured to emit light;

a receiving element configured to output an electrical signal in response to a reception of an acoustic wave from an object induced by the light;

a scanning unit configured to move the receiving element; and an amplifying unit configured to perform time gain control on the electric signal based on a relative position of the receiving element with respect to the object at reception of the acoustic wave by the receiving element.

With the object information acquiring apparatus of the present invention, it is possible to suppress variation in contrast of generated image in the object information acquiring apparatus that receives an acoustic sound while scanning a probe.

Further features of the present invention will become apparent from the following description of exemplary embodiments with reference to the attached drawings.

BRIEF DESCRIPTION OF THE DRAWINGS

FIG. 2 is an operation flowchart in the first embodiment;

DESCRIPTION OF THE EMBODIMENTS

Figure 1:
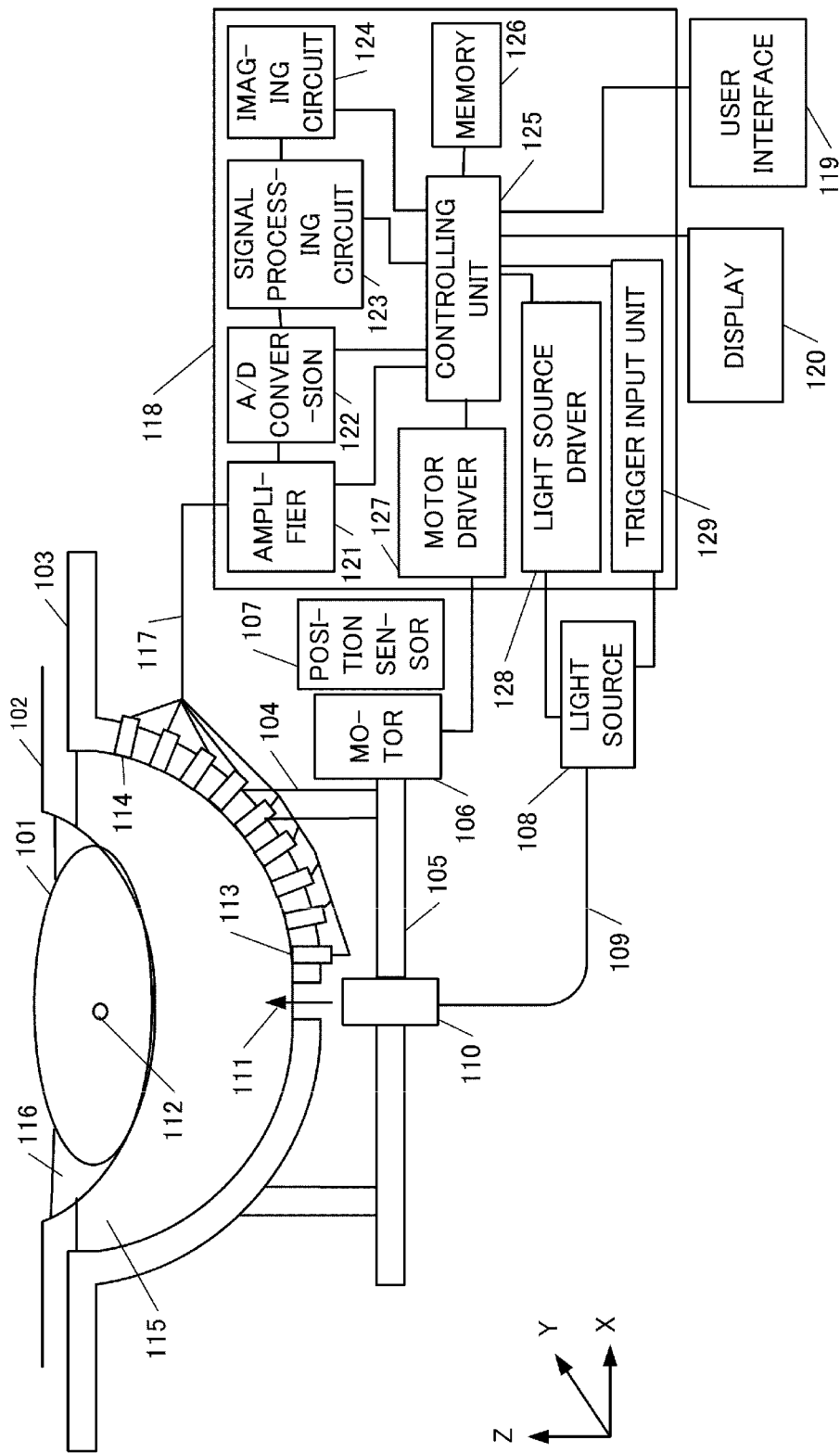
FIG. 1 is a block diagram in a first embodiment.

A preferred embodiment of the present invention is explained below with reference to the drawings. However, the dimensions, the materials, the shapes, a relative arrangement, and the like of components described below should be changed as appropriate according to the configuration and various conditions of an apparatus applied with the invention and are not meant to limit the scope of the present invention to the description explained below.

The present invention relates to a technique for detecting an acoustic wave propagated from an object, generating characteristics information on the object interior, and acquiring the characteristics information. Therefore, the present invention is understood as an object information acquiring apparatus or a control method therefor, an object information acquiring method, or a signal processing method. The present invention may also be understood as a computer program for causing an information processing apparatus including hardware resources such as a CPU to execute these methods or a storage medium having the computer program stored therein. The present invention may also be understood as an acoustic wave measuring apparatus or a control method therefor.

The present invention can be applied to an object information acquiring apparatus that makes use of a photoacoustic tomography technique for irradiating light (an electromagnetic wave) on an object and receiving (detecting) an acoustic wave generated in a specific position in the object or on the surface of the object and propagated according to a photoacoustic effect. The apparatus obtains characteristics information on the object interior in a form of image data, characteristics distribution information, or the like on the basis of photoacoustic measurement. Therefore, the object information acquiring apparatus may be called photoacoustic imaging apparatus or photoacoustic image-forming apparatus or simply called photoacoustic apparatus.

Characteristics information in the photoacoustic apparatus may be a generation source distribution of an acoustic wave generated by light irradiation, an initial sound pressure distribution in the object, an optical energy absorption density distribution or an absorption coefficient distribution derived from the initial sound pressure distribution, or a concentration distribution of a substance forming a tissue. Specifically, the characteristics information is an oxygenated/reduced hemoglobin concentration distribution, a blood component distribution such as an oxygen saturation degree distribution calculated from the oxygenated/reduced hemoglobin concentration distribution, a distribution of fat, collagen, or moisture, or the like. The characteristic information may be calculated as distribution information on positions in the object rather than as numerical value data. That is, distribution information on the absorption coefficient distribution, the oxygen saturation degree distribution, or the like may be set as object information.

The present invention can also be applied to an apparatus that makes use of an ultrasonic echo technique for transmitting an ultrasonic wave to an object, receiving a reflected wave (an echo wave) reflected on the inside of the object, and acquiring object information as image data. In the case of the apparatus that makes use of the ultrasonic echo technique, object information to be acquired is information reflecting a difference in acoustic impedance of tissues on the inside of the object.

The acoustic wave in the present invention is typically an ultrasonic wave and includes an elastic wave called sound wave or acoustic wave. An acoustic wave generated by the photoacoustic effect is referred to as photoacoustic wave or photo ultrasonic wave. An electric signal converted from the acoustic wave by the probe is referred to as acoustic signal. Acoustic signal deriving from the photoacoustic wave is particularly referred to as photoacoustic signal.

A breast of an organism may be assumed as the object in the present disclosure. However, the object is not limited to this. Measurement of other parts of the organism and non-organism materials are also possible.

First Embodiment

An apparatus according to a first embodiment of the present invention changes a gain of a photoacoustic signal according to the position of a probe at timing when the photoacoustic signal is received.

(Configuration and Functions of the Apparatus)

FIG. 1 shows an apparatus configuration in the first embodiment. In FIG. 1, reference numeral 101 denotes an object set as a measurement target and denotes a part of a body of a subject. The object 101 in this embodiment is a breast. Reference numeral 102 denotes an object holding member that holds the object 101 and specifies the shape of the object 101. As the object holding member 102, a material that transmits light and an acoustic wave is desirable. A thin film of polymethylpentene or the like molded in a bowl shape is suitably used. An object information acquiring apparatus desirably includes a coupling unit to which the bowl-shaped object holding member 102 is attached. If the object holding member 102 is used, a positional relation between receiving elements and points on the object holding member 102 is decided in advance for each of scanning positions of the probe. This is desirable in that a gain used for amplification can be calculated in advance and stored in a memory.

It is desirable to prepare bowl-shaped object holding members of a plurality of sizes different from one another and enable the object holding members to be replaced by the coupling unit according to a size of an object and a desired oppression thickness. Alternatively, a plurality of bowl-shaped holding members having different shapes one another may be prepared.

In these cases, a gain curve determined from the scanning position of the probe, the positions of the receiving elements, and the positions of the points on the holding member explained above is desirably stored in the memory according to a type of the holding member. A method of a controlling unit reading the type of the holding member set in the coupling unit is optional. For example, it is suitable to dispose an IC tag, a barcode, or the like on the holding member and use reading means corresponding to the IC tag, the barcode, or the like. A user may manually input the type of the holding member (or necessary information itself) when the user sets the holding member. The controlling unit reads out, from the memory, a gain corresponding to the read type of the holding member and determines the gain as a gain used for amplification processing.

Reference numeral 103 denotes a probe that receives an acoustic wave from the object 101 and converts the acoustic wave into a photoacoustic signal. The probe 103 has a configuration in which a large number of receiving elements are disposed on a spherical surface. The probe 103 can receive, from various angles, the acoustic wave received from the object 101. Reference numeral 104 denotes a supporting body that supports the probe 103. Reference numeral 105 denotes an XY stage that scans the probe 103 on an XY plane. The XY stage 105 is fastened to the probe 103 by the supporting body 104. Note that, in this embodiment, the vertical direction is represented as a Z axis and the horizontal surface is represented as the XY plane. Reference numeral 106 denotes a two-axis motor that drives the XY stage 105. As the two-axis motor 106, an AC servomotor, a stepping motor, or the like is used. Reference numeral 107 denotes a sensor for measuring the position of the XY stage 105. As the sensor 107, a potentiometer, an optical encoder, or the like is used. An XY coordinate of the probe 103 can be measured at accuracy of several ten micrometers. The XY stage 105 and the two-axis motor 106 configure a scanning unit in this embodiment. Specific components of the scanning unit are not limited to the components described above. A relative position of the probe 103 including the plurality of receiving elements with respect to the object 101 can be moved by the operation of the scanning unit.

Reference numeral 108 denotes a light source for generating pulsed light. The light source 108 is configured by a YAG laser, a titanium sapphire laser, or the like. The pulsed light source 108 includes a flash lamp and a Q switch as means for exciting a laser medium on the inside. Light emission timing of pulsed light source 108 can be electrically controlled from the outside. Reference numeral 109 denotes an optical path for guiding the pulsed light to near the object 101. The optical path 109 is configured using an optical system such as an optical fiber, a mirror and a bent arm, or the like. Reference numeral 110 denotes a light projecting unit that irradiates the pulsed light transmitted by the optical path 109 on the object 101. A diffusion plate is provided in the light projecting unit 110 to expand an irradiation range and reduce spatial intensity variation of the pulsed light. The light projecting unit 110 is fastened to the XY stage 105 and moves on the XY plane together with the probe 103.

Reference numeral 111 denotes the pulsed light emitted from the light projecting unit 110. Reference numeral 112 denotes a segment having large light absorption present on the inside of the object 101. For example, a newborn blood vessel due to breast cancer corresponds to the light absorbing segment 112. When the pulsed light 111 is irradiated on the light absorbing segment 112, energy of the pulsed light 111 is absorbed by the light absorbing segment 112. An acoustic wave is generated by the photoacoustic effect.

Reference numerals 113 and 114 denote receiving elements provided in the probe 103. The receiving elements 113 and 114 convert the acoustic wave into an electric signal called photoacoustic signal. A plurality of the receiving elements are provided on the probe 103 having a spherical surface shape (a spherical cap shape). Directional axes (high-sensitivity reception directions) of the receiving elements are directed in the center direction of the spherical surface. A high-sensitivity region is formed in the vicinity of the center of a sphere including the spherical cap. It is assumed that one hundred twenty-eight receiving elements are provided in this embodiment. In FIG. 1, the receiving elements are drawn only in the right half of the probe 103. However, actually, the receiving elements are disposed over the entire spherical surface of the probe 103. Consequently, the receiving elements receive, from various directions, the photoacoustic wave generated by the light absorbing segment 112 in the object 101 and reduce variation in resolution.

Note that the shape of the probe 103 that supports the receiving elements is not limited to the spherical cap shape. The probe 103 only has to be capable of supporting the plurality of receiving elements such that reception directions of at least a part of the receiving elements are different. For example, a shape obtained by cutting an elliptical sphere, a shape obtained by combining a plurality of planes or curved surfaces, and the like can also be used. The probe 103 desirably can hold an impedance matching material explained below on the inside irrespective of the shape.

Reference numeral 115 denotes an impedance matching material that acoustically combines the probe 103 and the object holding member 102. As the material of the impedance matching material 115, liquid that has acoustic impedance close to the acoustic impedance of the object 101 and the receiving elements and transmits the pulsed light is desirable. Specifically, water, castor oil, gel, or the like is used. Reference numeral 116 denotes an impedance matching material for acoustically combining the object 101 and the object holding member 102. Like the impedance matching material 115, a material matching an organism is used as the impedance matching material 116.

Reference numeral 117 denotes a cable for propagating a photoacoustic signal from the receiving element group including the receiving elements 113 and 114 to a control unit. Reference numeral 118 denotes a control unit. The control unit 118 receives the photoacoustic signal and performs processing such as amplification, A/D conversion, signal processing, and image reconstruction. The control unit 118 generates a driving signal for the motor 106 on the basis of a signal received from the position sensor 107. The control unit 118 sends a driving signal for the light source 108 in synchronization with the driving of the motor 106 and performs light emission of the pulsed light.

Reference numeral 119 denotes a user interface for the user to perform setting of operation conditions of the photoacoustic apparatus and an operation start instruction. The user interface 119 is configured by a keyboard, a mouse, button switches, and the like. The operation conditions include a measurement range of the object 101 and a reception time of a photoacoustic signal. Operation instructions include a start and suspension of photographing of the object 101. Reference numeral 120 denotes a display for displaying a diagnostic image to the user and notifying the user of a state of the object information acquiring apparatus.

Components of the control unit 118 are explained. An amplifier 121 is a circuit that amplifies a photoacoustic signal. The amplifier 121 is configured by a programmable gain amplifier array of 128 channels. The amplifier 121 in the present invention can change a gain for each of the channels according to setting from a controlling unit 125. Value set in the programmable gain amplifiers in order to change the gain is referred to as gain setting values. The controlling unit 125 determines, for each of the channels, a gain corresponding to the position of the probe 103 and sets a gain setting value for obtaining the gain in registers in the programmable gain amplifiers. The respective channels amplify signals from the respective receiving elements at set gains in analog domain. The amplifier 121 corresponds to an amplifying unit in this embodiment. Note that, in this specification, performing at least any one of processing for determining a gain, processing for amplifying a signal using the gain, and processing incidental to these kinds of processing is referred to as control of the gain.

Reference numeral 122 denotes a circuit that digitizes an analog signal amplified by the amplifier 121. The circuit 122 is configured from an A/D converter of 128 channels. A band of the A/D converter is wider than a bandwidth of the receiving elements and is desirably 30 MHz or more. Reference numeral 123 denotes a circuit that applies signal processing such as noise removal and averaging to a signal digitized by the A/D converter. The circuit 123 is configured by an FPGA or the like. The FPGA reads out output data from the A/D converter 123 of 128 channels in order and, after performing signal processing, records the output data in a memory 126 as photoacoustic signal data.

Reference numeral 124 denotes a circuit that applies image reconstruction processing and rendering processing to the photoacoustic signal data stored in the memory 126. The circuit 124 is configured by a GPU and the like. The imaging circuit 124 can be called a processing unit that acquires characteristics information on the interior of the object 101. For the image reconstruction, a publicly-known algorithm such as a universal back propagation (UBP) method is used. Reference numeral 125 denotes a control circuit (a controlling unit) that performs control of the entire apparatus. The controlling unit 125 is configured by microprocessor and software.

Figure 5A:
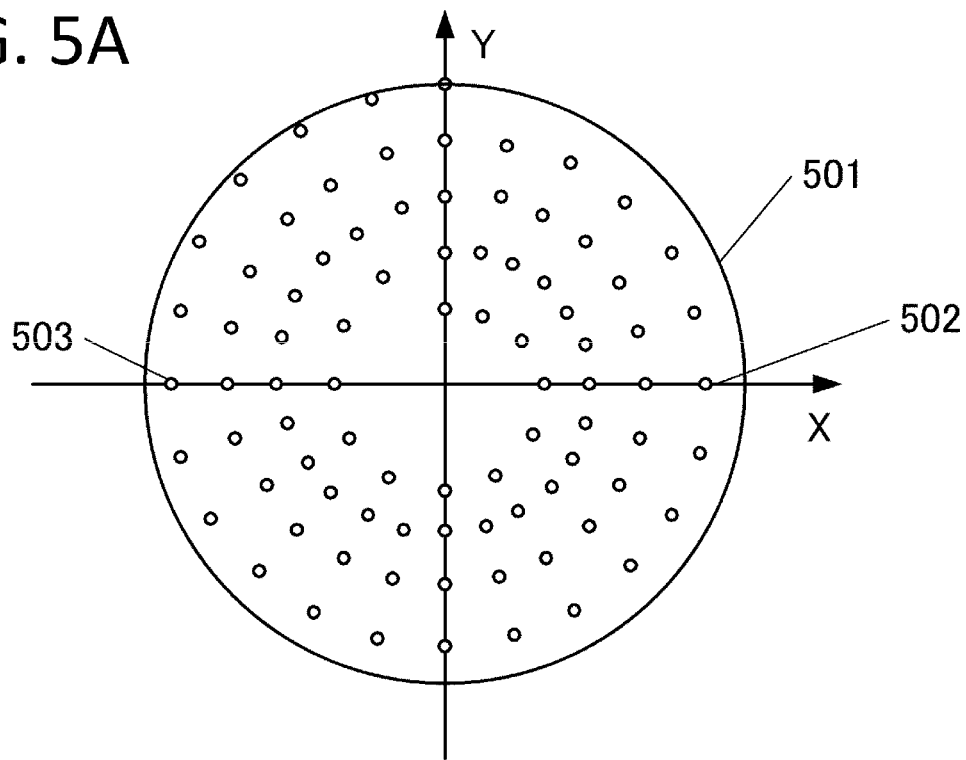
FIGS. 5A and 5B are diagrams showing examples of measurement coordinates and measurement regions in the first embodiment.
Figure 5B:
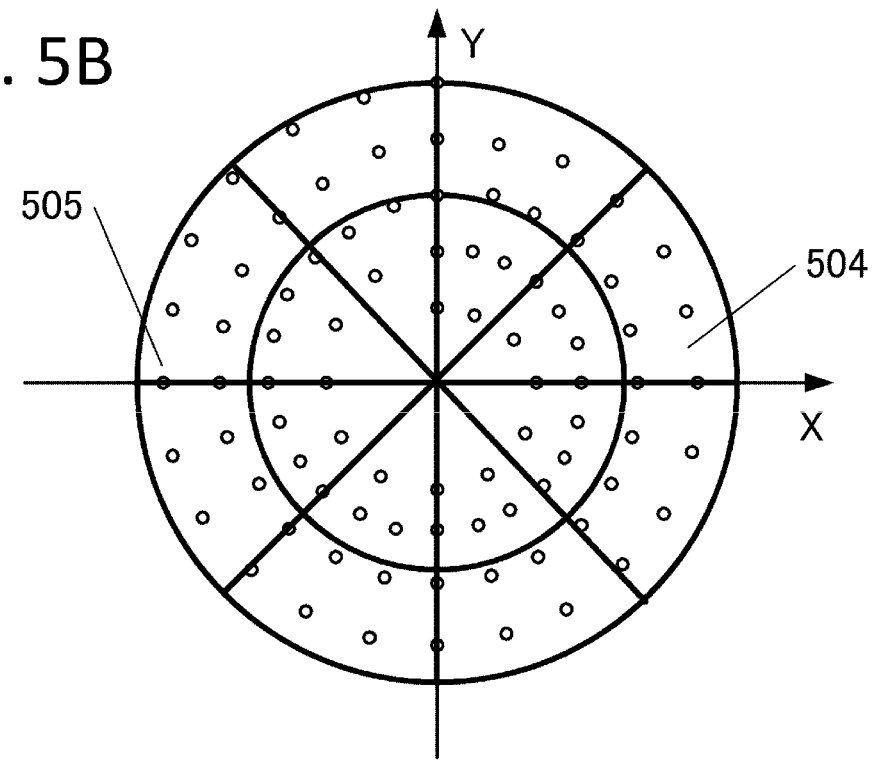

Reference numeral 127 denotes a driver circuit that generates a driving signal for the motor 106 on the basis of a command from the controlling unit 125 and position information on the XY stage 105 received from the position sensor 107. The controlling unit 125 calculates a target coordinate group that covers a measurement range designated by the user and sets the target coordinate group in the motor driver 127. An example of the measurement range and the target coordinate group is shown in FIG. 5A. FIG. 5A is a view of the probe seen through from the upper side of the object 101. The inside of a circle 501 is the measurement range. Points 502, 503, and the like in the measurement range 501 are target coordinates. As shown in FIG. 5A, the target coordinates are uniformly distributed in the measurement range. The motor driver 127 moves the probe 103 and the light projecting unit 110 to the target coordinates. The scanning unit may be considered as including the motor driver 127. According to the movement, a relative position of the probe 103 including the receiving elements with respect to the object 101 changes. An acoustic wave can be received in various places and directions.

A light source driver 128 is a driver circuit that generates a driving signal for the light source 108 on the basis of an instruction from the controlling unit 125. In causing the light source 108 to emit light, first, the light source driver 128 transmits a flash lamp driving signal and excites the laser medium inside the light source 108. Subsequently, when the light source driver 128 transmits a Q-switch driving signal after approximately 150 microseconds, sudden oscillation occurs inside the light source 108. Pulsed light having width of approximately 10 nanoseconds is output. When this is repeated at a fixed cycle, the light source 108 irradiates the pulsed light having a stable light amount on the object 101. In this embodiment, the cycle is 50 milliseconds. The light source 108 includes an actinometer and a shutter on the inside and also includes functions of monitoring of a light amount and an irradiation stop.

Reference numeral 129 denotes a circuit that receives a part of the pulsed light output from the light source 108 and generates a trigger signal for synchronizing with photoacoustic reception and motor driving. The trigger input unit 129 is configured from a photodiode, an amplification circuit, a comparison circuit, and the like. When the pulse light is input, the trigger input unit 129 outputs a trigger signal that changes to a high level for a period of several microseconds. The configuration of the trigger input unit 129 is not limited to this. A member including a function of a photosensor that detects light can be used. The control operation by the controlling unit 125 is performed starting from a point when the trigger input unit 129 detects light emission timing of the pulsed light. Consequently, it is possible to suppress the influence of variation in a delay time of each of pulses inside the light source 108 from the transmission of the Q-switch driving signal until the pulsed light is actually output.

The motor driver 127 controls the motor 106 such that the light projecting unit 110 and the probe 103 pass a target coordinate of the object 101 at light emission timing of a laser. At this point, the motor driver 127 synchronies the movement of the XY stage 105 with the trigger signal that changes to the high level at a cycle of 50 milliseconds. The motor driver 127 reads out a measurement coordinate from the position sensor 107 at timing when the trigger signal is input. The measurement coordinate is used for position correction of the probe 103 when the imaging circuit 124 performs the image reconstruction. Consequently, even when there is a shift between the target coordinate and the measurement coordinate because of a limit of driving accuracy of the XY stage 105, it is possible to reduce the influence of a diagnostic image.

The controlling unit 125 controls a gain of the amplifier 121 for each of the channels according to time after the trigger signal changes to the high level and a positional relation between the probe 103 and the object 101 and corrects attenuation of an acoustic wave. This is equivalent to changing the gain stepwise during reception of a photoacoustic wave. Specifically, the controlling unit 125 sets the gain low for a photoacoustic signal from a shallow position of the object 101 to prevent an output voltage of the amplifier 121 from being saturated. The controlling unit 125 sets the gain high for a feeble photoacoustic signal from the depth of the object 101 to prevent the photoacoustic signal from being buried in noise.

An attenuation amount of a photoacoustic wave from the object 101 changes according to a difference in the positions of the receiving elements. Therefore, in the present invention, the controlling unit 125 changes a gain for each of the receiving elements, that is, for each of the channels. For example, the controlling unit 125 uses different gains in amplification of the receiving element 113 and amplification of the receiving element 114. A positional relation between the receiving elements and the object 101 changes and an attenuation characteristic of the photoacoustic wave changes according to the position of the probe 103 driven by the XY stage 105. Therefore, the controlling unit 125 changes the gain for each of the measurement coordinates. The measurement coordinate is measured by the position sensor 107.

The controlling unit 125 controls the A/D converter 122, the signal processing circuit 123, and the imaging circuit 124. Consequently, A/D conversion, signal processing, and imaging is applied to signals input to the amplifier 121 within a predetermined time after the trigger signal changes to the high level. Results of the A/D conversion, the signal processing, and the imaging are stored in the memory 126.

The controlling unit 125 estimates a size of the object 101 in advance and determines the predetermined time such that a signal from a most distant position is included in the signals. The predetermined time is referred to as signal reception time Ts.

Operation Flow

FIG. 2 shows an operation flow of the object information acquiring apparatus executed by the control unit 118.

In step S201, the controlling unit 125 reads setting information set by the user via the user interface 119 and records the setting information in the memory 126 on the inside. As the setting information, there are the number of times of repeated irradiation in the same measurement point, a measurement range, a wavelength of pulsed light, and the like.

Subsequently, in step S202, the controlling unit 125 drives the motor 106 via the motor driver 127 and moves the probe 103 and the light projecting unit 110 on the XY stage 105 to a target coordinate.

Subsequently, in step S203, the controlling unit 125 calculates gain setting values of the receiving elements on the probe 103 on the basis of a coordinate measured by the position sensor 107 and stores the gain setting values in the memory 126. A data format of the gain setting values is a three-dimensional table information including combinations of channel numbers of the programmable gain amplifiers of the amplifier 121, time, and the gain setting values.

By arranging gain setting values of the channels in continuous memory addresses for each update time of a gain, it is possible to read out the gain setting values of the channels for each update time continuously and at high speed. Time when the gain is updated is determined in advance. Only the gain setting value at the time is stored. The time is referred to as gain update time. Consequently, only information necessary for the gain update is stored in the memory 126. Therefore, the capacity of the memory 126 can be reduced. The gain update may be repeated at a fixed cycle. An update frequency may be set high at time when a rate of change of a gain curve is large and set low at time when the rate of change is small. A calculation method for the gain curve is explained below.

Subsequently, in step S204, the controlling unit 125 accesses the amplifier 121 and changes the setting of the programmable gain amplifiers of the channels to obtain the gain calculated in step S203.

Subsequently, in step S205, the controlling unit 125 drives the light source 108 via the light source driver 128 to emit pulsed light having the wavelength set in step S201. Consequently, the pulsed light is irradiated on the object 101 by the light projecting unit 110. A photoacoustic wave is generated from the light absorbing segment 112 inside the object 101. The photoacoustic wave is converted into a photoacoustic signal by the receiving elements disposed on the probe 103 and input to the amplifier 121. Since the photoacoustic signal is feeble, the photoacoustic signal is amplified with the gain set in step S204.

On the other hand, a part of the pulsed light is split at the optical path 109 and input to the trigger input unit 129. As a branching method, a part of handle fiber may be divided or a beam splitter may be inserted. The emitted light of the pulsed light is converted into a trigger signal by the photosensor of the trigger input unit 129 and input to the controlling unit 125. By detecting light emission timing of the pulsed light in this way, even when time from the transmission of the driving signal to the light source 108 by the light source driver 128 until the pulsed light is actually output changes because of variation of the light source 108, the control unit 118 can grasp generation timing of the photoacoustic wave.

Subsequently, in step S206, the controlling unit 125 sends control signals to the A/D converter 122 and the signal processing circuit 123 and performs digitization and signal processing of the photoacoustic signal. As the signal processing, the controlling unit 125 performs filtering, wavelet conversion, noise removal processing such as averaging, and weighting processing for sensitivity variation correction of the receiving elements.

Subsequently, in step S207, the controlling unit 125 determines, with a timer circuit on the inside, whether time for updating the gain has come. In a case the time for updating the gain has come, the controlling unit 125 proceeds to step S208. In a case the time for updating the gain has not come, the controlling unit 125 proceeds to step S206, amplifies the photoacoustic signal with the same gain, and continues the digitization and the signal processing.

In step S208, the controlling unit 125 accesses the memory 126 and reads out gain setting values of the channels corresponding to time when the controlling unit 125 accesses the memory 126. The controlling unit 125 accesses the amplifier 121 and changes the setting of the programmable gain amplifiers of all the channels on the basis of the read-out gain setting values.

Subsequently, in step S209, the controlling unit 125 determines whether the signal reception time Ts has elapsed after the trigger signal is input. In a case the signal reception time Ts has elapsed, the controlling unit 125 proceeds to step S210. In a case the signal reception time Ts has not elapsed, the controlling unit 125 proceeds to step S206 and continues to perform reception of a photoacoustic signal.

In step S210, the controlling unit 125 determines whether the reception of the photoacoustic signal in all measurement positions covering the measurement range of the object 101 read in step S201 is completed. In a case the reception of the photoacoustic signal is completed, the controlling unit 125 proceeds to step S211. In a case the reception of the photoacoustic signal is not completed, the controlling unit 125 proceeds to step S202, moves the probe 103 to the next target coordinate, and repeatedly executes step S203 and subsequent steps.

Subsequently, in step S211, the controlling unit 125 reads out photoacoustic signal data from the memory 126, transfers the photoacoustic signal data to the imaging circuit 124, and performs image reconstruction processing. Consequently, a diagnostic image is created and stored in the memory 126.

Subsequently, in step S212, the controlling unit 125 reads out the diagnostic image from the memory 126 and causes the display 120 to display the diagnostic image.

Gain

Calculation and setting of a gain are explained with reference to FIGS. 3A to 5B.

FIGS. 3A to 3D are diagrams showing examples of gain curves and temporal changes of gain setting values corresponding to the receiving element 113 and the receiving element 114 on the probe 103.

Figure 4A:
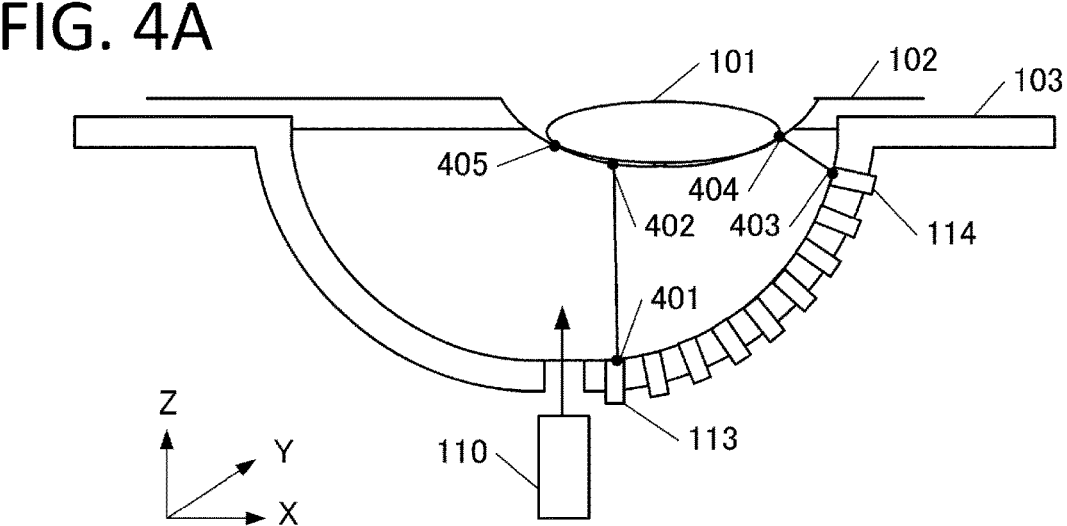
FIGS. 4A and 4B are diagrams showing positional relations between a probe and an object in the first embodiment.
Figure 4B:
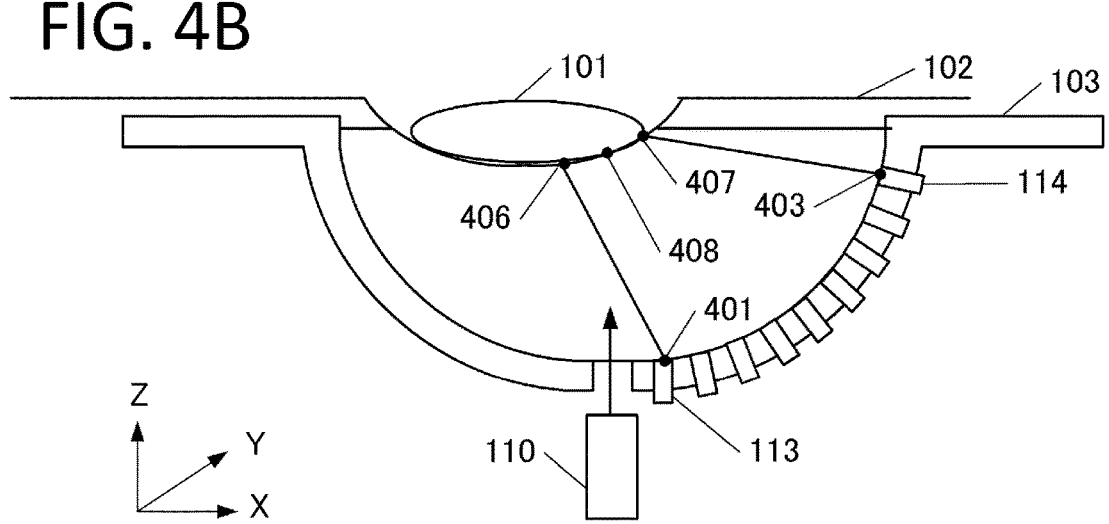

FIGS. 4A and 4B are diagrams showing positional relations between the probe 103 and the object 101 at points in time in certain two measurement coordinates. In FIG. 4A, the probe 103 moves to a negative side on an X axis and irradiates the vicinity of the left end of the object 101. This is a state in which the vicinity of the target coordinate 503 is irradiated in FIG. 5A. In FIG. 4B, the probe 103 moves to a positive side on the X axis and irradiates the vicinity of the right end of the object 101. This is a state in which the vicinity of the target coordinate 502 is irradiated in FIG. 5A.

In FIG. 4A, reference numeral 401 denotes a center point of the receiving element 113. Reference numeral 402 denotes a point on the object holding member 102 closest from the point 401. Reference numeral 403 denotes a center point of the receiving element 114. Reference numeral 404 denotes a point on the object holding member 102 closest from the point 403. Reference numeral 405 denotes an irradiation point on which pulsed light is irradiated from the light projecting unit 110.

In FIG. 4B, reference numeral 406 denotes a point on the object holding member 102 closest from the point 401. Reference numeral 407 denotes a point on the object holding member 102 closest from the point 403. Reference numeral 408 denotes an irradiation position. The pulsed light is irradiated on the vicinity of the irradiation position 408 from the light projecting unit 110. In this way, a shortest distance from the receiving elements to the points on the holding member is calculated.

Figure 3A:
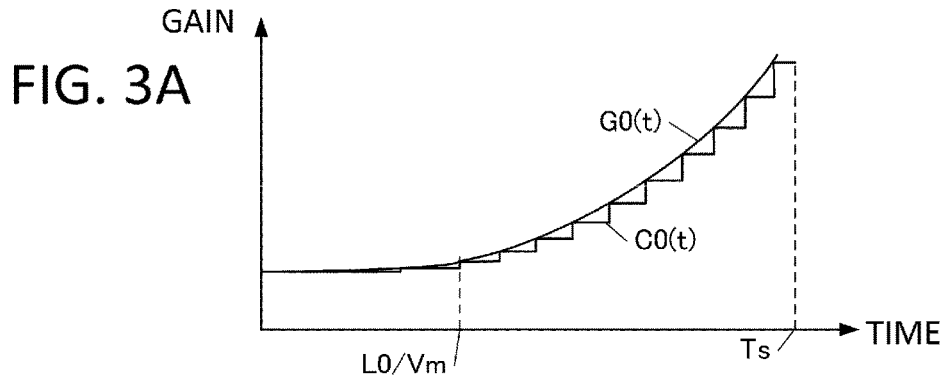
FIGS. 3A to 3D are diagrams showing examples of gain setting in the first embodiment.

FIG. 3A shows a gain curve $G0(t)$ of the receiving element 113 and a temporal change $C0(t)$ of a gain setting value set in the programmable gain amplifier corresponding to the receiving element 113 of the amplifier 121 in the case in which a positional relation between the probe 103 and the object 101 is as shown in FIG. 4A.

Figure 3B:
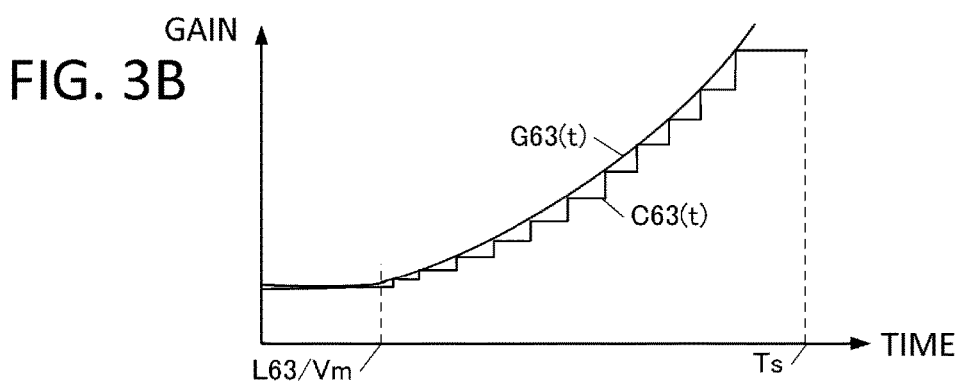

FIG. 3B shows a gain curve $G63(t)$ of the receiving element 114 and a temporal change $C63(t)$ of a gain setting value set in the programmable gain amplifier corresponding to the receiving element 114 of the amplifier 121 in the case in which the positional relation between the probe 103 and the object 101 is as shown in FIG. 4A.

Figure 3C:
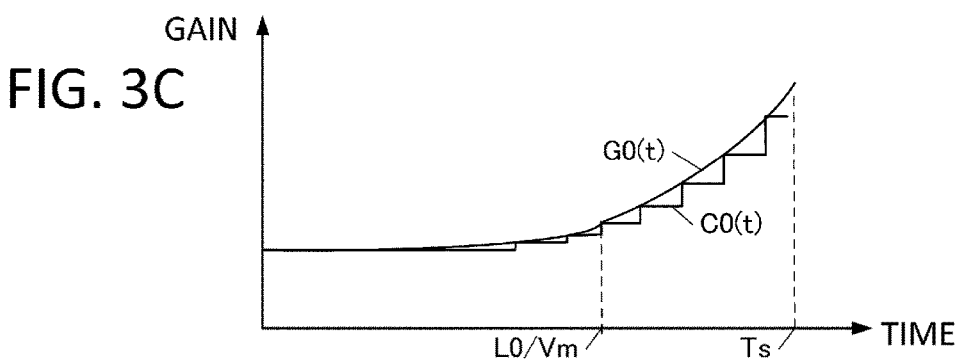

FIG. 3C shows the gain curve $G0(t)$ of the receiving element 113 and the temporal change $C0(t)$ of the gain setting value set in the programmable gain amplifier corresponding to the receiving element 113 of the amplifier 121 in the case in which the positional relation between the probe 103 and the object 101 is as shown in FIG. 4B.

Figure 3D:
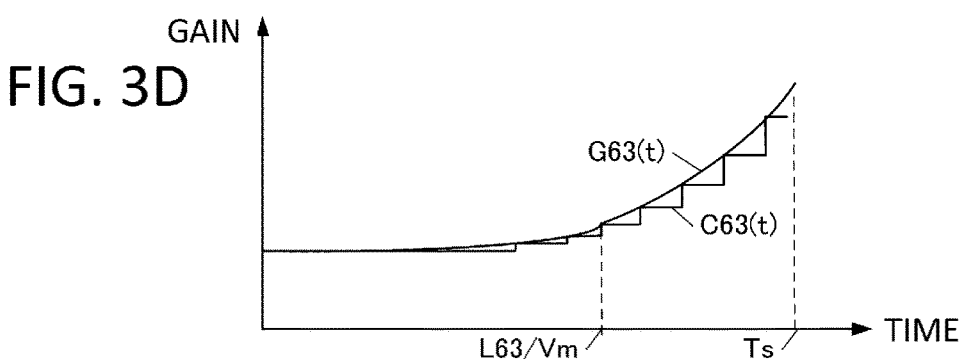

FIG. 3D shows the gain curve $G63(t)$ of the receiving element 114 and the temporal change $C63(t)$ of the gain setting value set in the programmable gain amplifier corresponding to the receiving element 114 of the amplifier 121 in the case in which the positional relation between the probe 103 and the object 101 is as shown in FIG. 4B.

The gain calculating step in step S203 is explained more in detail.

In step S203, the controlling unit 125 deduces a positional relation between the probe 103 and the object holding member 102 from the measurement coordinate and calculates distances from the receiving elements such as the receiving elements 113 and 114 to the object holding member 102. Numbers of the receiving elements are represented as N (N=0, 1, 2, . . . , and 127).

For explanation, an element number of the receiving element 113 is represented as 0 and an element number of the receiving element 114 is represented as 63. When the measurement coordinate is represented as (X, Y) and the distance from a receiving element with the element number N to the surface of the object holding member 102 is represented as Ln, Ln is a function determined by the shapes and attachment positions of the probe 103 and the object holding member 102, the measurement coordinate (X, y), and the element number N. This function is indicated by the following Expression (1):

$$Ln = \text{Function}(X, Y, N) \quad (1)$$

When the positional relation between the probe 103 and the object 101 is a state shown in FIG. 4A, L0 represents the distance between the point 401 and the point 402 and L63 represents the distance between the point 403 and the point 404. When the positional relation between the probe 103 and the object 101 is a state shown in FIG. 4B, L0 represents the distance between the point 401 and the point 406 and L63 represents the distance between the point 403 and the point 407.

When sound speed of an acoustic wave propagated in the impedance matching material 115 is represented as Vm and an attenuation rate of the acoustic wave is represented as Dm. Sound speed of the acoustic wave propagated in the object 101 is represented as Vs and the attenuation rate of the acoustic wave is represented as Ds. Time when the trigger signal changes to the high level is represented as 0. Note that a degree of attenuation of the acoustic wave is exponential.

When it is assumed that the sound speed is fixed in media, from time 0 to time Ln/Vm, a gain curve Gn(t) of the receiving element with the element number N is represented by the following Expression (2). Note that the gain curve is a curve indicating a relation between acquisition time t of a photoacoustic signal and a gain of each of the receiving elements. The gain curve is a curve of an inverse characteristic of attenuation of a photoacoustic wave. The gain curve reduces variation in photoacoustic signal data caused by the attenuation of the photoacoustic wave during propagation to the probe 103.

$$Gn(t) = A*\text{Exp}(Dm*t) \quad (2)$$

$(0<=t<=Ln/Vm)$

On the other hand, after time Ln/Vm, the gain curve Gn(t) of the receiving element is represented by the following Expression (3):

$$Gn(t) = A*(\text{Exp}(Ds*(t-Ln/Vm))-1) + A*\text{Exp}(Dm*Ln/Vm) \quad (3)$$

$(Ln/Vm<=t)$

A is a predetermined constant such that the programmable amplifiers of the amplifier 121 are not saturated. Note that, when irradiation intensity of light changes according to a position, a different value may be used as A according to the element number and the position of the probe 103. For example, the value of A may be set large for the receiving elements close to the irradiation points 405 to 408 of light and set small for the receiving elements far from the irradiation points of light. Irradiation intensity of light for each of the measurement coordinates may be calculated in advance by a simulation or the like and the value of A may be changed for each of XY coordinates.

When time of generation of the acoustic wave is represented as time 0, time Ln/Vm is equivalent to timing when an acoustic wave from the object 101 reaches the receiving elements. That is, an electric signal based on the acoustic wave received before this timing derives from the impedance matching material 115. An electric signal based on the acoustic wave received after this timing derives from the inside of the object 101. The time of the generation of the acoustic wave can be identified as light irradiation time in the case of the photoacoustic measurement in this embodiment. In the case of ultrasonic echo measurement, calculation needs to be performed taking into account time in which ultrasonic waves transmitted from the receiving elements reach the object 101 and time required for reflection of the ultrasonic waves from the object 101.

As explained above, the gain curve Gn(t) is the function of Ln and changes according to the receiving element numbers and the positional relation between the probe 103 and the object 101. The gain curve Gn(t) changes before and after time Ln/Vm according to a difference between attenuation rates of the acoustic wave of the impedance matching material 115 and the object 101.

As explained above, $G0(t)$ and $G63(t)$ at the time when the positional relation between the probe 103 and the object 101 is as shown in FIG. 4A are respectively shown in FIG. 3A and FIG. 3B. $G0(t)$ and $G63(t)$ at the time when the positional relation between the probe 103 and the object 101 is as shown in FIG. 4B are respectively shown in FIG. 3C and FIG. 3D.

A value of time Ln/Vm also changes according to the receiving element numbers and the positional relation between the probe 103 and the object 101. When the positional relation between the probe 103 and the object 101 is as shown in FIG. 4A, the distance between the receiving element 113 and the object 101 is long and the distance between the receiving element 114 and the object 101 is short. Therefore, L0/Vm in FIG. 3A is a value larger than L63/Vm in FIG. 3B.

On the other hand, when the positional relation between the probe 103 and the object 101 is as shown in FIG. 4B, the distance between the receiving element 113 and the object 101 and the distance between the receiving element 114 and the object 101 are substantially the same. Therefore, L0/Vm in FIG. 3C is a value close to L63/Vm in FIG. 3D. As explained above, the amplifying unit performs the processing for acquiring, on the basis of the positional relation between the receiving element and the object 101, time when the receiving element starts reception of the acoustic wave and applying a gain at least since when the reception has started.

The gain updating step in step S207 and step S208 is explained more in detail.

The controlling unit 125 periodically accesses the amplifier 121 and updates the gain on the basis of the gain curve Gn(t) within a range in which the programmable gain amplifiers can be set. A gain of the programmable gain amplifier of the channel corresponding to the receiving element with the receiving element number N in the amplifier 121 is represented as Cn(t). Cn(t) is updated in every gain update time by a value of Gn(t) at the time.

G0(t) and C63(t) at the time when the positional relation between the probe 103 and the object 101 is as shown in FIG. 4A are respectively shown in FIG. 3A and FIG. 3B. C0(t) and C63(t) at the time when the positional relation between the probe 103 and the object 101 is as shown in FIG. 4B are respectively shown in FIGS. 3C and 3D. As shown in FIGS. 3A to 3D, Cn(t) is a step-like function, a value of which changes in every gain update time. When a frequency of the update is high, a shift between Cn(t) and Gn(t) decreases and a change in contrast before and after the update becomes smooth. On the other hand, when the frequency of the update is low, the shift between Cn(t) and Gn(t) increases and a change in contrast becomes conspicuous before and after the update. Therefore, it is desirable to parallelize calculations of the receiving elements by providing a dedicated circuit in order to perform the update at high speed and reduce variation in the contrast. It is also desirable to provide a large-capacity memory and store calculation results of Ln of the receiving elements in all the target coordinates in the memory in advance.

Rather than using different gains in all of the one hundred twenty-eight receiving elements, a plurality of receiving elements disposed in the vicinity can be gathered as one receiving element group and the same gain can be used in the receiving element group. Consequently, since the frequency of the update decreases, it is possible to reduce a gain update load on the controlling unit 125 and hardware such as the memory 126. In this case, Ln is calculated on the basis of a coordinate of the center of receiving element groups and a gain is determined for each of the receiving element groups. For example, if four receiving elements disposed in the vicinity are regarded as one group, compared with when gains are updated for all the receiving elements, it is possible to reduce the hardware such as the memory 126 to a quarter. On the other hand, when the gain update load on the controlling unit 125 and the hardware such as the memory 126 are the same, it is possible to reduce an updating time interval to a quarter and increase the update frequency.

As explained above, according to the first embodiment, by changing the gain according to the positional relation between the probe 103 and the object 101, it is possible to correct intensity variation of the photoacoustic signals from the receiving elements due to the positional relation. Consequently, it is possible to reduce contrast variation of a diagnostic image. By changing the gain of the amplifier 121 as in this embodiment, even when a degree of attenuation of a signal is large and photoacoustic signal intensity greatly changes between a shallow segment and a deep segment in the object 101, an effect of a reduction of the contrast variation of the diagnostic image is obtained.

In particular, when the probe 103 having the spherical cap shape (or a shape in which reception directions of at least a part of the receiving elements are different) is used as in the first embodiment, the distances between the surface of the object holding member 102 and the receiving elements change according to scanning. Therefore, unlike when the object 101 is compressed by a plate and scanned by a probe in which elements are displayed in a two-dimensional array shape, arrival times of an acoustic wave from the object 101 to the receiving elements are different for each of the receiving elements. When TGC processing is performed using a gain common to the receiving elements in such a configuration, it is likely that accuracy in acquiring characteristics information such as image data is deteriorated. Therefore, by using the configuration of the first embodiment, it is possible to give appropriate gains to the receiving elements and perform the TGC processing.

Modifications

Note that, in the first embodiment, the value measured by the position sensor 107 after the probe movement is used as the coordinate of the probe 103 used for the calculation of the gain. However, a target coordinate on which light is irradiated may be determined in advance and stored in the memory 126 and the target coordinate stored in the memory 126 may be used for the calculation of the gain. Rather than performing the calculation of the gain while moving the probe 103, correspondence between the target coordinates and the gain setting values may be calculated in advance and stored in the memory 126 and, in step S203, the gain setting value only has to be read out from the memory 126. By performing a part of processing beforehand in this way, it is possible to reduce a processing load on the controlling unit 125 during photographing.

In the first embodiment, the example is explained in which feedback control is performed using the servo motor and the position sensor 107 for the driving of the XY stage 105. However, a driving method is not limited to this. For example, it is also possible to perform open loop control using a stepping motor or the like and omit the position sensor 107.

In the first embodiment, the gain curve is calculated using the two attenuation rates, i.e., the attenuation rate of the acoustic wave in the impedance matching material 115 and the attenuation rate of the acoustic wave of the object 101. However, a type of the gain curve is not limited to this. For example, when there are a plurality of impedance matching materials, the gain curve may be calculated using three or more attenuation rates. A complicated gain curves corresponding to characteristics of the structure of the inside of the object 101 may be calculated or a gain curve input by the user on the basis of the characteristics of the structure of the object 101 may be used. When the attenuation rate of the acoustic wave in the impedance matching material 115 is small with respect to the attenuation rate of the acoustic wave in the object, Dm may be set to 0 to simplify the gain curve.

In the first embodiment, the example is explained in which the update of the gain is also performed from time 0 to time Ln/Vm. However, a signal received in this section may be regarded as a signal from the outside of the object 101 and the gain may not be updated to reduce a load of the gain update processing.

It is also conceivable to set the gain to 0 from time 0 to time Ln/Vm and set the gain to a fixed value after time Ln/Vm. Consequently, the update of gains of the receiving elements is performed only once at time Ln/Vm. Therefore, it is possible to further reduce the gain calculation and update processing load.

The update of the gain may be performed when the position of the probe 103 changes in step S202 and the gain between time 0 and Ts may be set to a fixed value for each of the receiving elements to further reduce the load of the gain update processing.

In the first embodiment, the different gains are set for all the receiving elements. However, for example, the receiving elements may be divided into gain regions divided by bold lines in FIG. 5B and the same gain may be used in measurement coordinates in the same gain region. For example, in FIG. 5B, a gain same as a gain in a measurement coordinate 502 may be used in measurement coordinates in a gain region 504 and a gain same as a gain in a measurement coordinate 503 is used in measurement coordinates in a gain region 505. Consequently, compared with when gains are updated in all measurement coordinates, it is possible to reduce the gain update load on the controlling unit 125 and the capacity of the memory 126.

In the first embodiment, the example is explained in which the gain is updated at the stage when the time decided by the gain update time elapses. However, the gain may be updated in synchronization with the position of the probe 103. For example, the gain is updated when a coordinate measured by the position sensor 107 crosses a boundary of the gain regions shown in FIG. 5B. Consequently, compared with when the gain is updated at a fixed cycle, it is possible to reduce the gain update load on the controlling unit 125 and the capacity of the memory 126.

These gain regions are not fixed and can also be changed according to setting by the user and the size of a measurement region.

In the first embodiment, the correction of the photoacoustic signal attenuation corresponding to the positional relation between the probe 103 and the object 101 is realized by the gain control of the programmable gain amplifiers in the amplifier 121. However, a place where the gain is controlled is not limited to the amplifier 121. For example, digital values from the receiving elements after A/D conversion in a signal processing circuit may be multiplied with a gain calculated from the gain curve. In this case, the signal processing circuit corresponds to the amplifying unit. When the image reconstruction of a photoacoustic signal stored in the memory 126 is performed, the photoacoustic signal may be multiplied with a gain in an image processing circuit. In this case, the image processing circuit corresponds to the amplifying unit. In these methods, limitation that the gain setting values are set stepwise because of the update time of the gain of the programmable gain amplifiers is reduced. It is possible to more finely change the gain.

In the first embodiment, the object 101 is fixed and the probe 103 and the light projecting unit 110 two-dimensionally move. However, in the scanning, the probe 103 and the light projecting unit 110 may be fixed and the object 101 may move. In the first embodiment, the probe 103 and the light projecting unit 110 move together. However, the probe 103 and the light projecting unit 110 may separately move or one of the probe 103 and the light projecting unit 110 may be fixed. The example is explained in which the probe 103 two-dimensionally moves on the XY plane. However, the probe 103 may move in the Z-axis direction.

In the first embodiment, the pulsed light from the light source 108 is detected by the photosensor of the trigger input unit 129. The gain curve is calculated and the driving of the motor 106 and the photoacoustic reception are performed starting from time when the pulsed light is detected. However, the gain curve may be calculated and the driving of the motor 106 and the photoacoustic reception maybe performed starting from time when the controlling unit 125 transmits a driving signal to the light source driver 128. Consequently, it is possible to omit the trigger input unit 129 when delay times of the light source 108 and the light source driver 128 are known and reduce a circuit size.

In the first embodiment, the gain is controlled according to the shortest distance from the receiving elements to the points on the object holding member 102. However, the present invention is not limited to this as long as the distances from the receiving elements to the object 101 can be calculated. For example, as a configuration in which the object holding member 102 is not provided, a shape acquiring unit that acquires a three-dimensional shape of the object 101 may be provided. In this case, the shortest distance from the receiving elements to the points on the object surface is calculated by three-dimensional operation processing and the gain is controlled on the basis of a result of the three-dimensional operation processing. As the shape acquiring unit, a camera that optically acquires the three-dimensional shape is suitable. An acoustic wave may be transmitted and received between the receiving elements on the probe 103 and the object 101 to acquire the shape of the object 101.

As explained above, according to the embodiment of the present invention, by changing the gain according to the relative positions of the object 101 and the receiving elements that change during the scanning, attenuation until the acoustic wave reaches the receiving elements is compensated. Consequently, it is possible to reduce variation in contrast of the object information acquiring apparatus.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-172983, filed on Aug. 27, 2014, which is hereby incorporated by reference herein in its entirety.

What is claimed is:

1. An object information acquiring apparatus comprising:
   a probe supporting a plurality of receiving elements such that directivity axes of the plurality of receiving elements converge, each of the plurality of receiving elements configured to receive an acoustic wave, generated by irradiation of light onto an object, and to output an electric signal, the probe provided to be spaced apart from the object at measurement;
   an amplifying unit configured to amplify electric signals output from the plurality of receiving elements;
   a scanning unit configured to change relative positions of the probe with respect to the object;
   a controlling unit configured to determine time-dependent gains applied to the electric signals by the amplifying unit when the plurality of receiving elements receives the acoustic wave; and
   a processing unit configured to acquire characteristics information on the object, using the electric signals that have been amplified by the amplifying unit,
   wherein the controlling unit determines, for a plurality of relative positions of the probe with respect to the object, the time-dependent gains applied to the electric signals on a basis of distances between the plurality of receiving elements and the object.

2. The object information acquiring apparatus according to claim 1, further comprising a holding member that holds the object.

3. The object information acquiring apparatus according to claim 2, further comprising an opening to which the holding member is replaceably provided, and
   a memory in which a plurality of the time-dependent gains each corresponding to different types of the holding member are recorded,
   wherein the controlling unit acquires information concerning a type of the holding member used for holding the object, reads out, on the basis of the information concerning the type of the holding member, from the memory gains corresponding to the holding member used for holding the object, and determines the gains read out from the memory as the time-dependent gains of the amplifying unit so as to compensate for an attenuation of the acoustic wave.

4. The object information acquiring apparatus according to claim 2, wherein the holding member is a bowl-shaped holding member that holds the object.

5. The object information acquiring apparatus according to claim 2, wherein the controlling unit determines the time-dependent gains of the amplifying unit according to a distance from the receiving element to a closest point on the holding member.

6. The object information acquiring apparatus according to claim 5, wherein the controlling unit determines, according to a degree of attenuation of the acoustic wave received by the receiving element, the time-dependent gains applied to the electric signals by the amplifying unit, with the degree of attenuation being determined on the basis of the distance from the receiving element to the closest point on the holding member.

7. The object information acquiring apparatus according to claim 5, wherein the controlling unit determines the time-dependent gains such that the time-dependent gains applied to the electric signals by the amplifying unit before a time when the receiving element starts reception of the acoustic waves deriving from the object is different from the time-dependent gains after a time when the receiving elements start reception of the acoustic waves deriving from the object, the time being determined on the basis of the distance from the receiving elements to the closest point on the holding member.

8. The object information acquiring apparatus according to claim 5, wherein the controlling unit controls such that the amplifying unit applies the time-dependent gains to the electric signals from time when the receiving elements start reception of the acoustic waves deriving from the object, the time being determined on the basis of the distance from the receiving elements to the closest point on the holding member.

9. The object information acquiring apparatus according to claim 1, further comprising a memory in which gains corresponding to the positional relations between the probe and the object is recorded,
   wherein the controlling unit reads out the gain corresponding to the positional relation between the probe and the object from the memory and determines the gain read out from the memory as the time-dependent gain of the amplifier.

10. The object information acquiring apparatus according to claim 1, wherein the controlling unit calculates the time-dependent gain according to the positional relations between the probe and the object.

11. The object information acquiring apparatus according to claim 1, wherein the controlling unit determines the time-dependent gain for each of a plurality of groups of the receiving elements, the groups being determined according to positions of the elements within the probe.

12. The object information acquiring apparatus according to claim 1, wherein the controlling unit determines, according to an irradiation point of the light on the object and the positional relation between the probe and the object, a gain applied to the electric signal by the amplifying unit.

13. The object information acquiring apparatus according to claim 1, wherein the probe has a bowl shaped inner surface, and the plurality of receiving elements are disposed along the inner surface.

14. An object information acquiring apparatus comprising:
   a probe supporting a plurality of receiving elements such that directivity axes of the plurality of receiving elements converge, each of the plurality of receiving elements configured to output an electrical signal in response to a reception of an acoustic wave from an object induced by the light, the probe provided to be spaced apart from the object at measurement;
   a scanning unit configured to change relative positions of the probe with respect to the object; and
   an amplifying unit configured to perform time gain control on electric signals output from the plurality of receiving elements by applying time-dependent gains, the time dependent gains being determined based on distances between the probe and the object at reception of the acoustic waves by the receiving elements.

15. The object information acquiring apparatus according to claim 14, further comprising a memory in which gains corresponding to the positional relations between the probe and the object is recorded,
   wherein the amplifying unit applies the gain corresponding to the positional relation between the probe and the object recorded in the memory as the time-dependent gain.

16. The object information acquiring apparatus according to claim 14, wherein the time-dependent gain is determined according to the positional relations between the probe and the object.

17. The object information acquiring apparatus according to claim 14, wherein the time-dependent gain is determined for each of a plurality of groups of the receiving elements, the groups being determined according to positions of the elements within the probe.

18. The object information acquiring apparatus according to claim 14, wherein the gain applied to the electric signal by the amplifying unit is determined according to an irradiation point of the light on the object and the positional relation between the probe and the object.

19. An object information acquiring method comprising:
changing relative positions of a probe with respect to an object, wherein the probe supports a plurality of receiving elements such that directivity axes of the plurality of receiving elements converge, and wherein the probe is provided to be spaced apart from the object at measurement;
outputting an electrical signal, by each of the plurality of receiving elements, in response to a reception of an acoustic wave from the object induced by the light; and
performing time gain control on electric signals output from the plurality of receiving elements by applying time-dependent gains, the time dependent gains being determined based on distances between the probe and the object at reception of the acoustic waves by the receiving elements.

20. The object information acquiring method according to claim 19, further comprising reading out a gain corresponding to the positional relation between the probe and the object from a memory, wherein the memory stores gains corresponding to the positional relations between the probe and the object,
wherein performing time gain control on electric signals comprises applying the gain read out from the memory as the time-dependent gain.

21. The object information acquiring method according to claim 19, wherein the time-dependent gain is determined according to the positional relations between the probe and the object.

22. The object information acquiring method according to claim 19, wherein the time-dependent gain is determined for each of a plurality of groups of the receiving elements, the groups being determined according to positions of the elements within the probe.

23. The object information acquiring method according to claim 19, wherein the gain applied to the electric signal is determined according to an irradiation point of the light on the object and the positional relation between the probe and the object.

* * * * *